United States Patent [19]

Nomoto et al.

[11] Patent Number: 4,553,544
[45] Date of Patent: Nov. 19, 1985

[54] SUTURING INSTRUMENT FOR SURGICAL OPERATION

[75] Inventors: Reishi Nomoto; Masayoshi Takahashi, both of Kanagawa; Yoshikazu Ebata, Tokyo, all of Japan

[73] Assignee: Janome Sewing Machine Co. Ltd., Tokyo, Japan

[21] Appl. No.: 660,391

[22] Filed: Oct. 12, 1984

Related U.S. Application Data

[63] Continuation of Ser. No. 421,119, Sep. 20, 1982, abandoned.

[51] Int. Cl.[4] .......... A61B 17/06; D05B 97/00
[52] U.S. Cl. .................. 128/340; 112/169; 112/277; 128/334 R
[58] Field of Search .......... 128/334 R, 335, 339, 128/335.5, 334 C, 326, 340; 112/169, 185, 194–195, 277; 200/67 F

[56] References Cited

U.S. PATENT DOCUMENTS

| 2,573,499 | 10/1951 | Scott | 112/169 |
|---|---|---|---|
| 2,849,580 | 8/1958 | Tateishi | 200/67 F |
| 2,988,028 | 6/1961 | Alcamo | 112/169 |
| 3,138,393 | 6/1964 | Livingston | 285/277 |
| 3,665,872 | 5/1972 | Hodgins | 112/277 |
| 4,123,982 | 11/1978 | Bess, Jr. et al. | 112/169 |
| 4,235,177 | 11/1980 | Arbuckle | 112/169 |
| 4,406,237 | 9/1983 | Eguchi et al. | 112/169 |
| 4,414,908 | 11/1983 | Eguchi et al. | 112/169 |
| 4,417,532 | 11/1983 | Yasukata | 112/169 |

Primary Examiner—C. Fred Rosenbaum
Assistant Examiner—Gene B. Kartchner
Attorney, Agent, or Firm—Michael J. Striker

[57] ABSTRACT

A suturing instrument for surgical operations is operated by an operator with his one hand. A suturing operation is carried out on a human part to be sutured up by crossing a needle thread and a shuttle thread in a lock stitching formation, the instrument being composed of independent members which are, for use, connected to each other easily, exactly and speedily. The main body of the instrument carrying a needle and a shuttle has an externally operated actuating member which actuates a signal generator incorporated in a connecting arrangement for connecting the main body with the drive part of the instrument, whereby when the drive part is connected to the main body by the connecting arrangement an operator may, by moving the actuating member, activate the drive through the signal generator and set all the parts of the instrument into operating positions.

5 Claims, 10 Drawing Figures

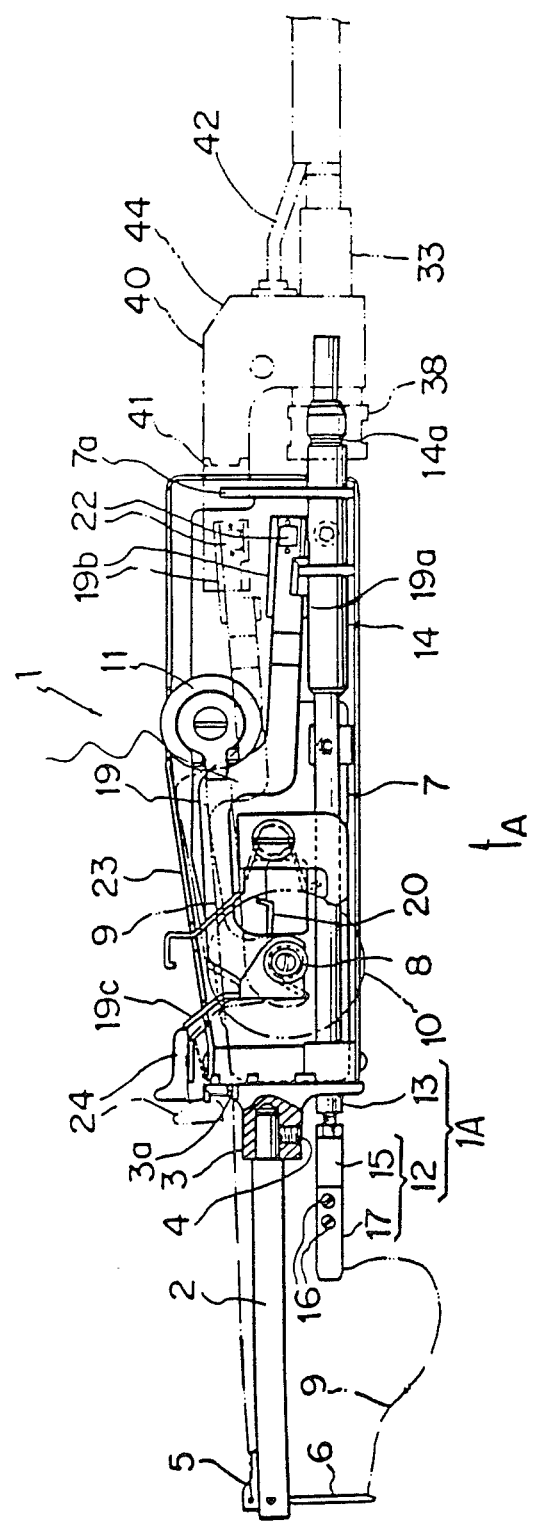
FIG_1

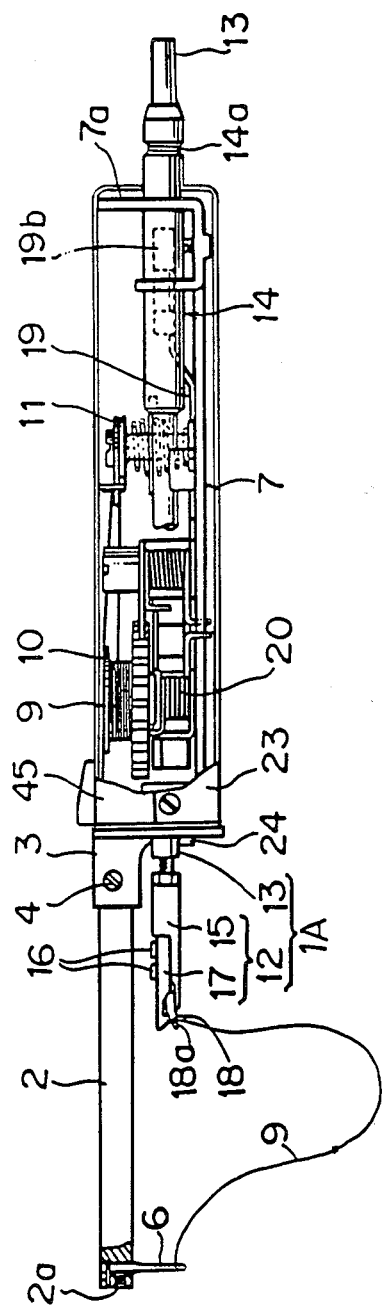
FIG_2

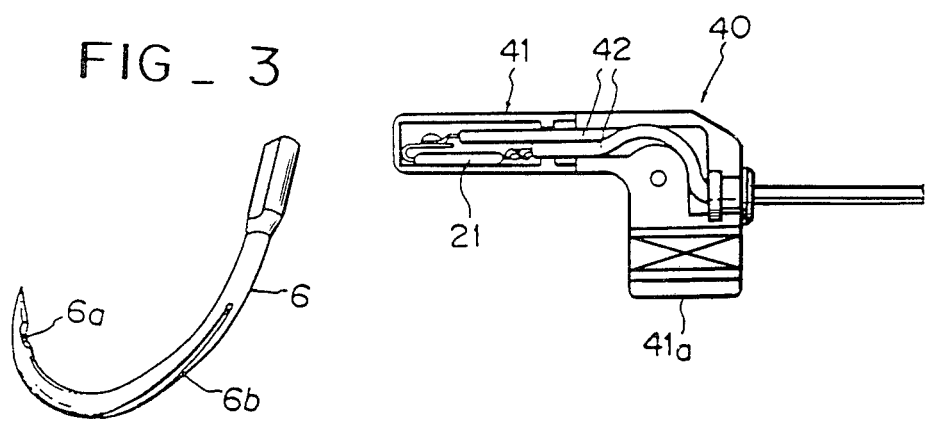
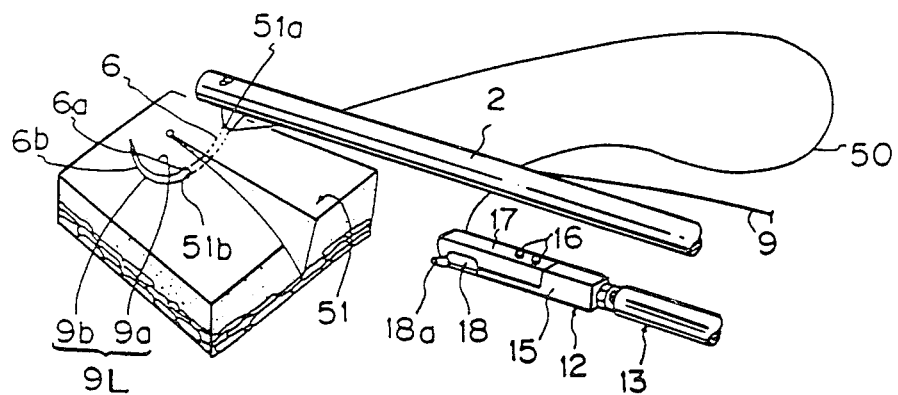

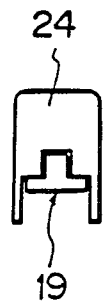
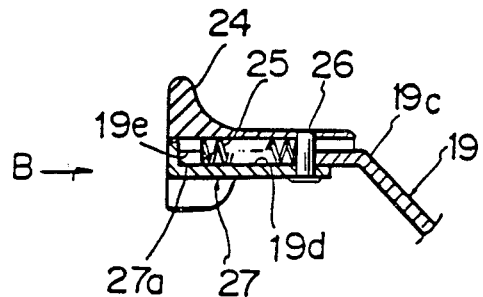
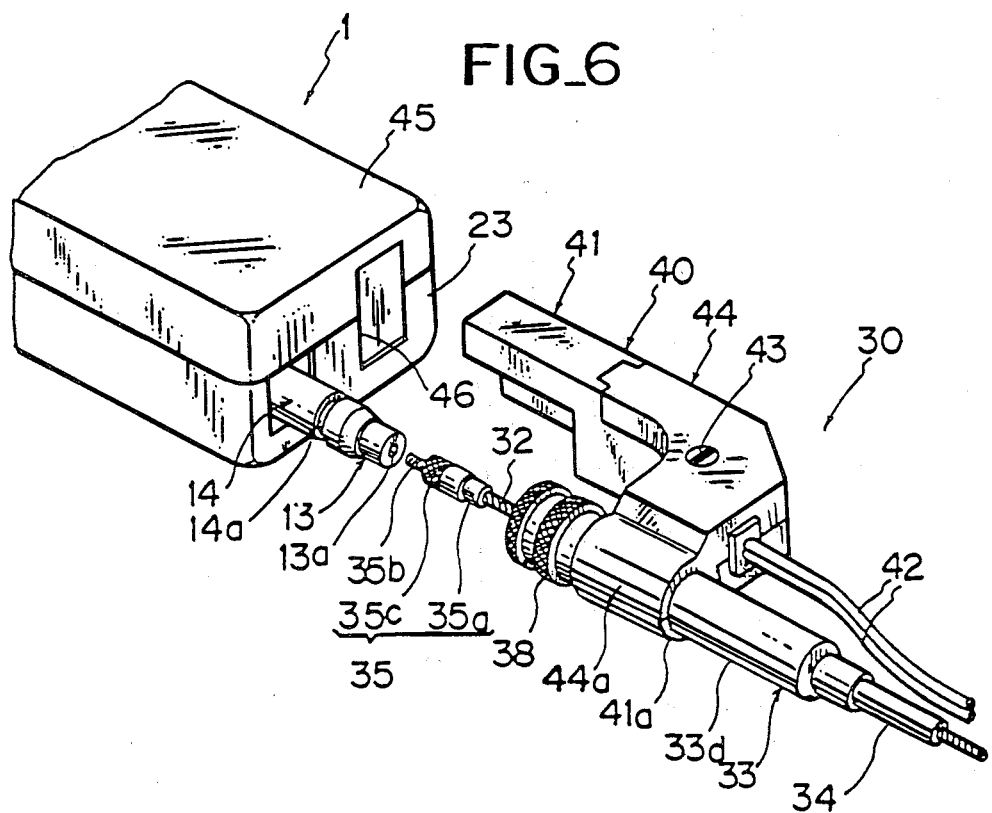

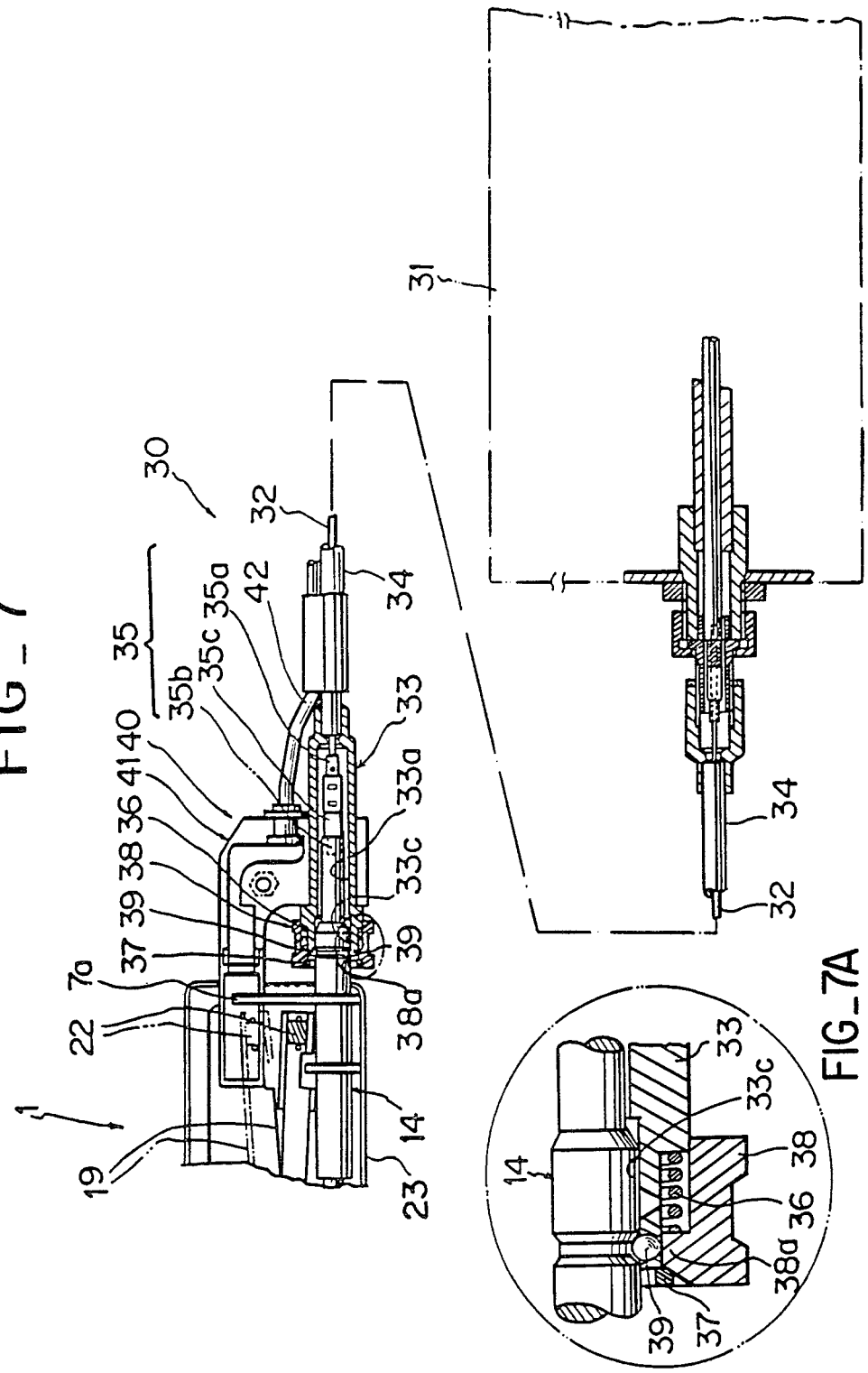
FIG_7
FIG_7A

SUTURING INSTRUMENT FOR SURGICAL OPERATION

This is a continuation of application Ser. No. 421,119 filed Sept. 20, 1982 now abandoned.

BACKGROUND OF THE INVENTION

The invention relates to a suturing instrument for surgical operation and is operated by an operator with his one hand; the suturing operation is carried out on a human part to be sutured up by crossing a needle thread and a shuttle thread in a lock stitching formation.

SUMMARY OF THE INVENTION

An object of the invention is to provide a suturing instrument for a surgical operation which is composed of respectively independent members of a suturing device, a drive part for driving a main body of the device, and connecting members which are provided with a signal line for transmitting a signal made by an external operation to the drive part and a flexible cable for transmitting an output of the drive part to be actuated by said signal to said main body of the suturing device, and wherein a signal switching member for generating said signal is incorporated inside of said connecting members; a control member for controlling the signal switching member is incorporated inside of the main body of all suturing device; and when the independent members are connected to each other for use of the device, the members are made ready for the operating relative positions, and the control member disposed at the main body of the suturing device is incorporated in an actuating member which may be operated externally, and the control member is moved by an operating member in the direction about perpendicular to the actuating direction of the actuating member, so that the operation by the operating member is enabled; and since the suturing main body is not included with a distributing wire such as switch and others, its main body may be solely washed and sterilized.

Another object of the invention is to provide a suturing instrument for surgical operations, wherein the signal generator at the connecting part is met with the guide part of the suturing main body for the connection of the suturing main body to the connecting part, whereby the flexible cable is connected only the side of the suturing main body to provide an operative condition. Thus, the connection and the disconnection can be rapidly effected, and undesirable connection can be solved, which occurred in connection with the leading wires.

A further object of the invention is to provide a suturing instrument for surgical operations wherein the signal switching member and the control member thereof are incorporated in the separate members so that the suturing device is prevented from erroneous operation and the operational safety may be heightened.

Another object of the invention is to provide a suturing instrument for the surgical operations, wherein the control member is operated by two step operation of the operating member to avoid the erroneous actuation.

BRIEF DESCRIPTION OF THE DRAWINGS

FIG. 1 is a plan view partially in section showing a main part of a suturing instrument;

FIG. 2 is a view seen from arrow A in FIG. 1, with a cover partially removed;

FIG. 3 is a perspective view of a curved needle;

FIG. 4 is a cross sectional view showing a relation between an actuating member and an operational member;

FIG. 5 is a view seen from arrow B in FIG. 4;

FIG. 6 is a perspective view showing a main body of the connecting member and a part of a suturing instrument.

FIG. 7 is a side view partially in section showing a main body of the connecting member and a part of the suturing instrument;

FIG. 7A is an enlarged sectional view seen at arrow F of FIG. 7;

FIG. 8 is a view showing a removed signal generator;

FIG. 9 is a perspective view of the parts of the instruments for explaining the suturing operation.

DETAILED DESCRIPTION OF THE PREFERRED EMBODIMENTS

The present invention will be explained in reference to the embodiment shown in the attached drawings. In FIGS. 1 and 2, the numeral 1 is a main body of a suturing device (called as "main body" hereafter), in which a needle bar 2 is secured at its one end to a needle bar supporter 3 with a screw 4, and is provided on the other end with a thread guide piece 5 and is connected detachably with a curved needle 6 by a screw 2a.

The curved needle 6 is, as seen in FIG. 3, provided with a needle eye 6a at its end portion and with a thread guiding long groove 6b extended from a half way of an outer part to the needle eye 6a.

Referring back to FIGS. 1 and 2, it is seen that a thread stand 8 is secured to a machine frame 7 of the main body 1, and is detachably mounted with a thread supply coil 10 with a suturing thread 9 wound thereon. The thread 9 is effected with tension device by a thread tension 11 of a conventional type provided on the machine frame 7, and is drawn through the thread guide groove 3a of the needle bar supporter 3, and guided in a thread guide piece 5 and the groove 6b of the curved needle 6 to the needle eye 6a and further to a thread hole 18a of a later mentioned shuttle 18.

1A generally denotes a shuttle holding member which comprises a shuttle holder device 12 and a rod 13. The rod 13 is slidably reciprocated together with the shuttle holder device 12 under a condition that the rod 13 is guided between a guide tube 14 secured to the machine frame 7 and the needle bar supporter 3 secured to the same, and is restrained with respect to rotation.

The shuttle holder device 12 comprises a shuttle holder 15 and a shuttle pawl 17 connected to the shuttle holder with a screw 16, so that a shuttle 18 does not drop.

An actuating member 19 is rotatably arranged with respect to the thread stand 8, and is biased in the clockwise direction in FIG. 1 around the thread stand 8 by means of a spring 20 whose one end is held to the actuating member 19 and the other is held to the machine frame 7, and an engaging part 19a of member 19 contacts an outer circumference of the guide tube 14 as shown with the solid line in FIG. 1.

On one end 19b of the actuating member 19 a permanent magnet 22 is provided for controlling a lead switch 21 as an embodiment of the signal switching a member (FIG. 8) for switching signal, which switch is mounted in the signal generator which will be explained below; on the other end 19c extending out of the cover 23 of the main body an operating member 24 is provided.

The operating member 24 is movable with respect to said end 19c of the actuating member 19 and, as seen in FIG. 4, is biased via a pin 26 to the right side in the same by a spring 25 location within a guide groove 19d for the actuating member 19. An engaging part 27a of a member 27 is fixed to the operating member 24 with a pin 26 and is contacted to an engaging face 19e of the actuating member.

If the operating member 24 is pressed toward action of the actuating member 19 under said condition, the operating member 24 contacts the side of the needle bar supporter 3 and cannot be operated, but if the actuating member 24 is pushed to the left at FIG. 1 in right angle with the operating member 19 against action of the spring 25, the operating member 19 may be operated by the actuating member 24, and under this condition if the member 24 is pushed to the main body, the operating member 19 may be rotated as shown with dotted line in FIG. 1.

A explanation will be now made to a connector 30 in reference to FIGS. 6 to 8. A flexible cable 32 is for transmitting an output of a drive part 31 to the main body 1, and its end is guided from page 31 to a flexible guide tube 34 which is connected to a connecting member 33 formed with a calking, and the end portion of cable 32 is secured to a rear part 35a of a connecting member 35.

The connecting member 35 comprises the rear part 35a and an end portion 35c which is rotatable with respect to said rear part and is formed with a screw 35b which is screwed into a female threaded part 13a defined in a rod 13 which extends through the guide tube 14 to the shuttle holding member 15 so that the connecting member 35 is connected to the rod 13. The connecting member 35 is structured such that it is reciprocated by a drive part 31 within the interior 33a (FIG. 7) of the connecting sleeve 33 and the guide tube 14 under the condition that it is connected to the rod 13.

The connecting sleeve 33 is biased by a spring 36 to the left side of FIG. 7, and is mounted with an outer annular ring 38 which is locked on sleeve 33 by a stopper ring 37. The outer annular ring 38 pushes balls 39 which are radially movably guided in a plurality formed in grooves of the connecting sleeve 33, toward the inner face of a tube portion 33c of the connecting sleeve 33 by means of an inner projection 38a on ring 38. The balls 39 are fitted within a groove 14a of a guide tube 14 as shown in FIG. 7 when a connecting body 30 and the main body 1 are connected.

A signal generator 40 is provided with a lower member 41, and a signal wire 42 which is connected to a lead switch 21 which is an embodiment of a signal switching member. The signal wire 42 drawn from the signal generator 40 is connected to the drive part 31. The signal generator 40 holds an outer part 33d (FIG. 6) of the connecting sleeve 33 by means of a holding part 41a of the lower member 41 and a holding part 44a of an upper part 44.

The numeral 7a (FIG. 1) in the main body 1 is a guide piece which guides the signal generator 40, together with a guide part 46 formed in common in the covers 23 and 45, of the main body 1 into latter when the main body 1 and the body 30 are connected.

With respect to the signal generator 40, when the actuating member 19 is rotated to the position shown with the dotted line in FIG. 1, the signal switching member 21 issues a signal, and the drive part 31 is driven via the signal wire 42 and the shuttle holder device 12 is reciprocated by a determined stroke via the flexible cable 32.

A further reference will be made FIG. 9 to explain to the actuation of the present suturing instrument. The suturing thread 9 is drawn out via the needle eye 6a from the main body 1 and is combined with a thread hole 18a of the shuttle 18 to make a shuttle thread 50. When the main body 1 is held by one hand of the operator and the curved needle 6 is penetrated into a penetration hole 51b of a part 51 to be sutured up, and a needle thread portion 9a is pulled in straight between the needle hole 6a and the pentration hole 51b as shown in FIG. 9 and forms a needle thread loop 9L of a crescent together with a needle thread portion 9b guided in the groove 6b.

When the operating member 24 is operated to rotate the actuating member 19 to the position shown by the dotted line as seen in FIG. 1, the signal switching member 21 issues a signal by the action of magnet 22, and the drive part 31 is driven via the signal wire 42, and the shuttle holding device 12 is reciprocated by a determined stroke together with the shuttle holder 15 via the flexible cable 32.

During this reciprocation, the needle shuttle loop 9L (FIG. 9) is passed between the shuttle pawl 17 and the upper surface of the shuttle 18 on the forward way in the reciprocating movement of the shuttle holder 15, and the shuttle loop 9L is passed between the shuttle holder 15 and the lower surface of the shuttle 18 on the backward way of the shuttle holder 15. Since the needle thread loop 9L and the shuttle thread 50 are crossed in the lock stitching manner, the curved needle 6 is drawn out from the penetration hole 51b, and the needle thread 9 and the shuttle thread 50 are tightened. Subsequently, penetrating holes are made on the part to be sutured up in succession along the suturing line.

The main body 1 is incorporated with the permanent magnet 22 serving as the control member, but since the main body is not incorporated with a distributing wire instrument such at the switch and others, the main body 1 of the suturing device may be solely washed and sterilized.

The main body 1 and the connecting to each other body 30 are connected by rotating a male screw 35b of the connecting member 35 to screw it at an end point 35c into a female threaded portion 13a of the rod 13, moving the outer ring 38 to the right in FIG. 7 against the action of the spring 36 with respect to the connecting sleeve 33, guiding the signal generator 40 into the guide part 46 and in the guide piece 7a so that the connecting sleeve 33 and the outer circumference of the guide tube 14 are fitted each other, and by moving the outer ring 38 by the hand to make a condition as shown in FIG. 7 due to the action of the spring 36 the balls 39 are pushed by the inner projection 38a and are engaged in the groove 14a. Thus, the connection of the main body 1 and the connecting body 30 is completed, and the signal switching member 21 is biased a predetermined position with respect to the control or magnet 22.

As mentioned above, since the connection between the main body 1 and the connecing body 30 are made operationally, the connection and the disconnection can be rapidly effected, and undesirable connection can be prevented which can occur in the case of the leading wires used in such connector.

With respect to the connection of the main body 1 and the connecting body 30, the signal switching member 21 is incorporated in a casing independently from the control member or magnet 22. Since the signal switching member 21 is not actuated by itself, the suturing device can be prevented from erroneous operation and the operational safety may be heightened. During use of the suturing device, the actuating member 19 is operated by pushing out the operating member 24 to the left side in FIG. 1 in the direction being right angled with the acting direction of the actuating member 19, against the action of the spring 25, and subsequently the operating member 24 is pushed into the main body 1. For providing the safety the two step operation is prepared.

What is claimed is:

1. A suturing instrument for surgical operations, comprising a main body; a needle guide connected to the main body and having a needle thereon carrying a suturing thread; a shuttle holder reciprocable within said main body and carrying a shuttle extended outwardly from said main body to receive the suturing thread from the needle and cooperating with the needle for forming on a human part to be sutured up lock stitches; drive means positioned outside said main body and being operative for reciprocating said shuttle holder; connecting means for connecting said drive means to said main body; actuating means including an operating member operated externally from said main body and an actuating member positioned in said main body and connected to said operating member to be rotated thereby; switch means including a control magnet member mounted on said actuating member inside said main body, and signal-generating means for producing a signal and adapted to be actuated by said control magnet; holding means accommodating said signal-generating means and positioned outside of said main body and being partially insertable thereinto so as to insert said signal-generating means into said main body, said holding means being connected to said connecting means outside of said main body; means for transmitting said signal from said switch means to said drive means; and cable means for transmitting an output of said drive means actuated by said signal to said main body to drive the latter, whereby said switch means can operate only when said holding means is partially inserted into said main body whereas said drive means can operate for reciprocating said shuttle holder only when said drive means are connected to said main body by said connecting means so that when the operating member is pushed by an operator relative to said actuating member the actuating member is rotated to move said control magnet of said switch means toward said signal-generating means to actuate the latter to cause the signal-generating means to actuate said drive means which will reciprocate said shuttle holder when said main body and said drive means are connected to each other by said connecting means and when said holding means is partially inserted into said main body.

2. The instrument as defined in claim 1, wherein said actuating member is spring-biased in said main body.

3. The instrument as defined in claim 2, further including a guide tube mounted in said main body and having one end connected to said shuttle holder and an opposite end connectable to said connecting means.

4. The instrument as defined in claim 3, wherein said means for transmitting the signal to the drive means is a signal wire connecting said signal generator to said drive means.

5. The instrument as defined in claim 4, wherein said connecting means further include a connecting member having one end connected to said cable means and another end connectable to said guide tube, a slidable connecting sleeve adapted to surround said connecting member when said main body and said drive means are connecting to each other by said connecting means, an annular ring surrounding said connecting sleeve, and balls interpositioned between said annular ring and said connecting sleeve such that said ring is clamped on said sleeve when the instrument is in its operating position.

* * * * *